United States Patent [19]

Kyle

[11] 4,220,813
[45] Sep. 2, 1980

[54] TERMINAL FOR MEDICAL INSTRUMENT
[75] Inventor: James C. Kyle, Mission Viejo, Calif.
[73] Assignee: Medical Components Corp., Mission Viejo, Calif.
[21] Appl. No.: 836,657
[22] Filed: Sep. 26, 1977
[51] Int. Cl.[2] .................. H01B 17/26; A61N 1/36
[52] U.S. Cl. .................. 174/152 GM; 128/419 P
[58] Field of Search ............ 174/152 GM; 128/419 P; 361/30 Z

[56] References Cited

U.S. PATENT DOCUMENTS

| 1,906,816 | 5/1933 | Schmidt, Jr. | 174/152 GM |
| 3,320,557 | 5/1967 | Garstang | 361/302 X |
| 3,920,888 | 11/1975 | Barr | 174/152 GM |
| 4,072,154 | 2/1978 | Anderson et al. | 128/419 P |
| 4,152,540 | 5/1979 | Duncan et al. | 174/152 GM |

Primary Examiner—Roy N. Envall, Jr.
Assistant Examiner—E. F. Borchelt
Attorney, Agent, or Firm—Ellsworth R. Roston

[57] ABSTRACT

A terminal is provided for introducing signals from an electrical terminal pin in a heart pacemaker to a terminal lead introduced into a patient's body. The terminal pin is disposed in a lid of the heart pacemaker so that the terminal pin is insulated from the lid. Means are also provided for introducing the signals on the terminal pin to the terminal lead without subjecting the pin to undue stresses.

The terminal includes a hollow, electrically conductive ferrule disposed in concentric relationship with the terminal pin. The ferrule is provided with a flange which is disposed against the lid. An electrical filter is disposed in the ferrule and means are provided for maintaining the filter in fixed relationship to the ferrule and the terminal. Insulating means are provided for bonding the ferrule and the terminal. An inductance may also be included in the terminal and may be connected to the filter to enhance the filtering effect.

An insulating bead is disposed on the ferrule and is bonded to the ferrule to transfer stresses on the terminal pin to the bead and ferrule. The insulating bead supports an electrically conductive catheter block which fits over the electrical terminal pin and communicates electrically with the terminal pin. The catheter block also holds the terminal lead in fixed position and communicates electrically with the lead and directs the lead into the body of the patient.

41 Claims, 6 Drawing Figures

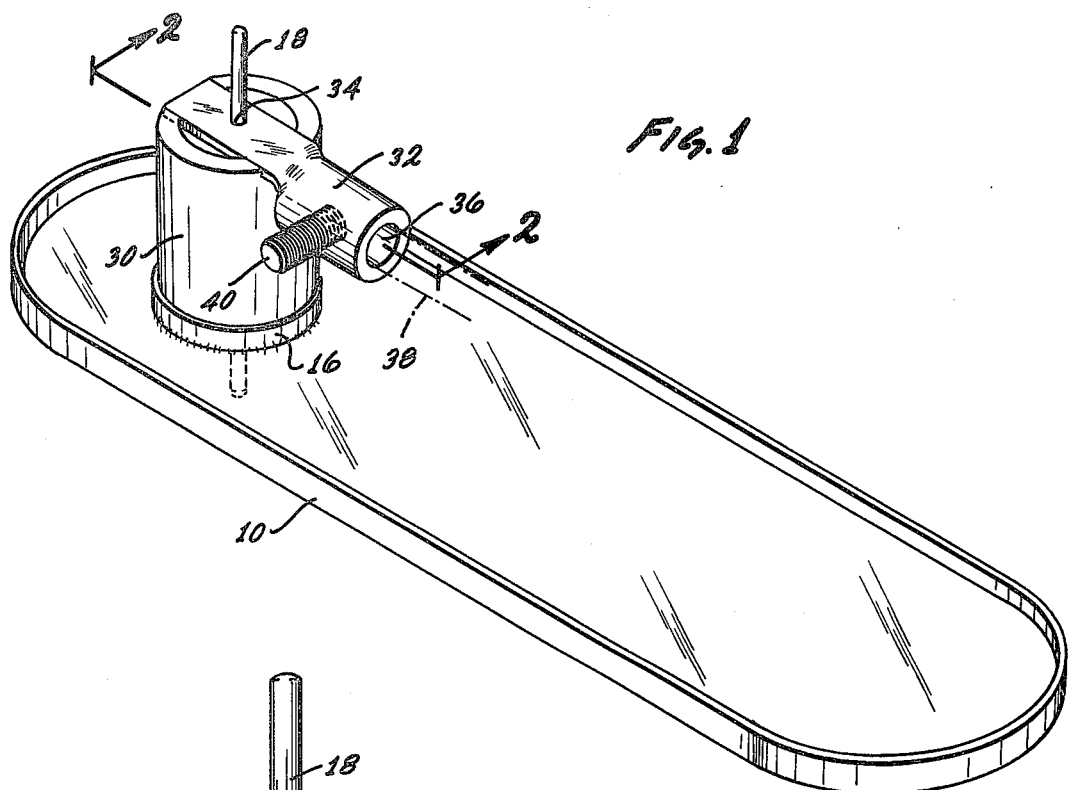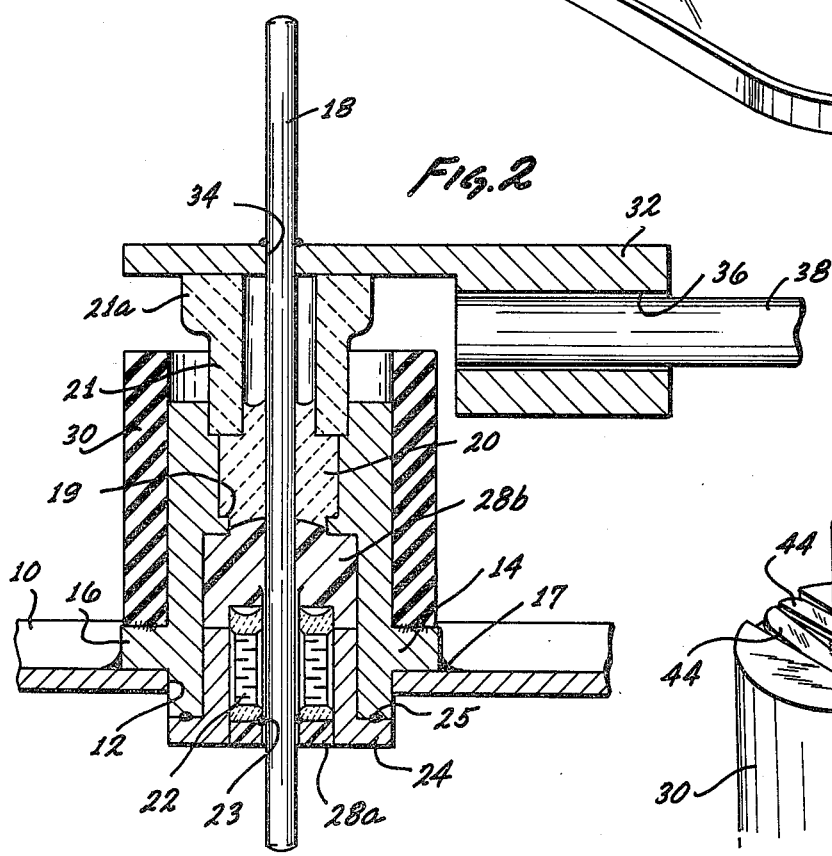

TERMINAL FOR MEDICAL INSTRUMENT

This invention relates to a terminal for maintaining an electrical terminal pin in insulated relationship to a lid on a housing for a heart pacemaker and for introducing signals from the electrical terminal pin to a terminal lead passing into the patient's body. More particularly, the invention relates to a terminal for maintaining the electrical terminal pin in insulated relationship to the lid and for providing for the introduction of signals from the terminal pin to the terminal lead without any bending or breaking of the terminal pin and without destroying the hermetic relationship produced in the terminal.

In recent years, considerable advances have been made in medical technology involving the treatments of patients with heart problems. For example, patients having defective hearts have received heart pacemakers which produce signals at a particular frequency and stimulate the heart so that the heart pumps blood through the patient at that frequency. Initially, the heart pacemakers were disposed externally. However, with recent advances in the construction of the heart pacemakers and in medical technology, the heart pacemakers are now often disposed within the body of the patient.

In spite of the considerable advances which have been made, some problems still exist in heart pacemakers. For example, the electrical terminal pin providing signals to the heart is still not disposed relative to the lid and housing of the heart pacemaker so that a hermetic seal is maintained between the terminal pin and the lid. As will be appreciated, if a hermetic seal is not maintained between the terminal pin and the lid, the terminal pin will not be maintained in electrically insulated relationship to the lid so that the introduction of signals from the terminal pin to the heart of the patient deteriorates.

Another problem in heart pacemakers has been that the electrical terminal pins tend to become bent or broken when a catheter block has been inserted into the body of the patient to provide for the introduction of signals from the terminal through an electrical lead to the patient's heart. This has resulted in part because the electrical terminal pin has not been properly supported relative to the lid. When the terminal pins become bent, the insulating relationship between the terminal pin and the lid and the hermetic seal in the terminal tend to become destroyed. As a result, malfunctions of the pacemaker have occurred.

Considerable effort has been made to solve the problems discussed in the previous paragraphs. For example, a considerable effort has been made to insure that a hermetic seal is maintained between the electrical terminal and the lid when the heart pacemaker is inserted into a patient's body. A considerable effort has also been made to prevent the electrical terminal pin from becoming bent or broken and the hermetic seal in the terminal from becoming destroyed when a catheter block is inserted into the body of a patient and is coupled to the terminal pin. In spite of these considerable efforts, the problems discussed above still exist to a pronounced effect in heart pacemakers.

This invention provides a terminal which overcomes the problems discussed above. For example, the terminal of this invention provides and maintains a hermetic seal between the terminal pin and the lid to insure that the terminal pin is in electrically isolated relationship to the lid and that no leakage of fluid can occur into or out of the heart pacemaker. Furthermore, the apparatus provides for the insertion of a catheter block (or electrical body) into the body of a patient and for the coupling of the catheter block to the electrical terminal pin without bending or breaking the electrical terminal and without destroying the hermetic seal. In this way, the terminal of the invention insures that electrical signals are introduced, without any deterioration in quality, from the pacemaker into the patient's heart.

The apparatus includes a hollow, electrically conductive ferrule disposed in concentric relationship with the electrical terminal pin. The ferrule is provided with a flange which is disposed against the lid to maintain the ferrule in a particular relationship to the lid. An electrical filter is disposed in the ferrule to pass signals having only a particular frequency to the electrical terminal for introduction to the patient's heart. Means are provided for maintaining the filter in fixed and insulated relationship to the ferrule and the terminal pin. Insulating means are provided for bonding to the ferrule and the terminal pin.

An insulating bead is disposed on the ferrule in a particular relationship to the ferrule. The insulating bead supports a catheter block (or electrically conductive body) which fits over the electrical terminal pin and communicates electrically with the terminal pin. The catheter block also holds the terminal lead in fixed position and communicates electrically with the lead and directs the lead into the body of the patient.

In one embodiment, a compressible seal is disposed in the terminal and is compressed upon the assembly of the parts comprising the terminal. The compression of the seal facilitates the production of a hermetic relationship in the terminal. An inductance is disposed in the seal and is connected to the filter and the terminal pin to facilitate the filtering of signals introduced into the patient's body.

In the drawings:

FIG. 1 is a perspective view of a lid for the housing of a heart pacemaker and an electrical terminal for maintaining a terminal pin in the terminal in insulated relationship to the lid and for introducing signals from the pacemaker through the terminal pin and into the body of a patient;

FIG. 2 is a sectional view substantially on the line 2—2 of FIG. 1 and shows the terminal of FIG. 1 in further detail;

FIG. 3 is a perspective view of a modification of one of the features shown in the previous Figures;

Figure 4:
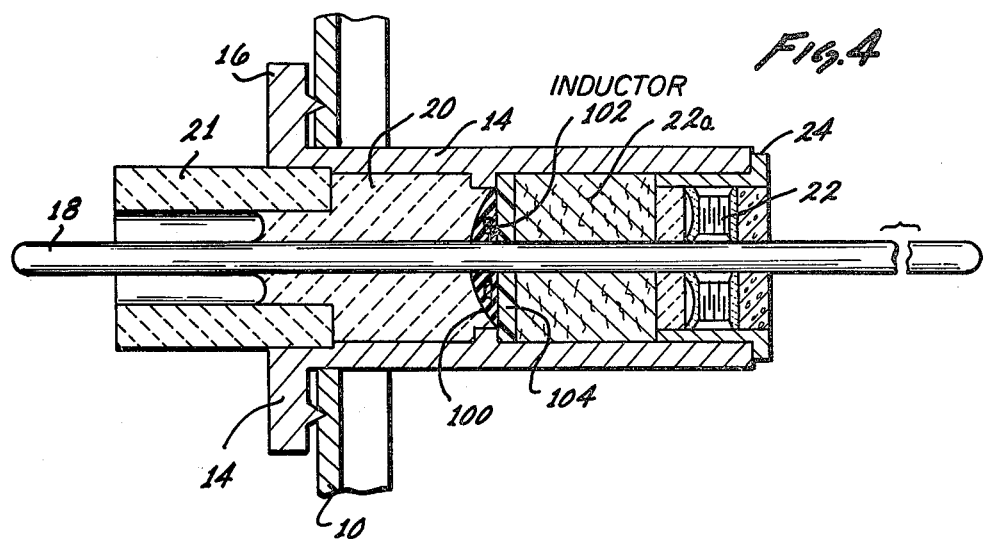
FIG. 4 is a sectional view similar to that of FIG. 2 but showing another embodiment of the invention.

In one embodiment of the invention, a lid 10 is provided with an aperature 12. A ferrule 14 having a hollow cylindrical configuration is disposed within the aperture 12 and is provided with a flange 16 which rests on the lid 10. The flange 16 of the ferrule 14 is welded as at 17 to the lid 10 around the periphery of the flange. The ferrule 14 may be made from a suitable material such as titanium or stainless steel.

An electrical terminal pin 18 made from a suitable material such as platinum is disposed within the ferrule 14 in concentric relationship to the ferrule. The terminal pin 18 is hermetically sealed to the ferrule 14 by a suitable material 20 which is seated on an internal flange 19 in the ferrule 14. The material 20 may constitute a standard glass-to-metal seal. Preferably, however, the material 20 may constitute a seal such as disclosed and claimed in application Ser. No. 836,659 filed by me on Sept. 26, 1977, for a "Ceramic Seal and Method of Making Such Seal" and assigned by me of record to the assignee of record of this application. Glass, and particularly the material disclosed in copending application Ser. No. 836,659, are advantageous because they provide a high electrical impedance, produce a long path for the flow of electrical leakage current between the ferrule 14 and the terminal pin 18 and maintain a hermetic seal between the pin and the ferrule even when the pin is subjected to considerable bending and twisting forces. The seal 20 is disposed in contiguous relationship to an internal flange on the ferrule 14.

The production of the hermetic seal may be facilitated by the inclusion of a ring or bead 21 between the insulating material 20 and the ferrule 14 at one end of the insulating material. The ring or bead 21 may be made from a suitable insulating material such as alumina. The ring or bead 21 is seated on an internal shoulder in the ferrule 14 and is fused to the insulating material 20. The ring or bead 21 is advantageous because it tends to increase considerably the length of the leakage path between the ferrule 14 and the terminal 18. In this way, any leakage of moisture between the terminal 18 and the ferrule 14 is minimized, as is any formation of dendrites as a result of such leakage.

An electrical filter 22 is also disposed on the terminal 18 within the hollow configuration of the ferrule 14. The filter 22 has characteristics for passing signals only in a range of approximately 10 megahertz. For example, the filter 22 may have 6 db characteristics at approximately 10 megahertz, 40 db characteristics at approximately 100 megahertz and 60 db characteristics at approximately 1 gigahertz. As shown in FIG. 2, the filter 22 may be disposed at least partially within the heart pacemaker. The filter 22 may be constructed in a conventional manner from a plurality of spaced plates or discs to define a capacitive filter. The filter 22 may be attached to the terminal pin 18 as by solder at 23.

The filter 22 is maintained in fixed relationship within the ferrule 14 by a spacer 24 made from a suitable material such as a stainless steel (if the ferrule is made of stainless steel) or made of nickel or a nickel-iron-cobalt alloy designated by the trademark "Kovar" (if the ferrule is made of titanium). The spacer 24 is provided with a hollow cylindrical body and with a flange which is disposed against the bottom of the ferrule 14. The spacer 24 is attached to the ferrule 14 at 25 as by projection welding. Projection welding is desirable since it provides localized heating without affecting the solder attachment 23.

A suitable adhesive such as a thermal-setting epoxy is disposed as fillers 28a and 28b on opposite sides of the filter 22 to maintain the filter in fixed position relative to the ferrule. The epoxy may be purchased commercially. For example, a commercially granulated epoxy may be purchased from Hysol in Pasadena, Calif., for use as the epoxy materials 28a and 28b. The filler 28b is disposed at one end against the internal flange 19 on the ferrule 14.

A sleeve 30 made from a suitable insulating material such as alumina or a polysulfide is disposed on the flange 16 of the ferrule 14 and is bonded to the ferrule by the application of heat at a particular temperature of approximately 600° F. The sleeve 30 has properties of being relatively inert from a chemical standpoint and being relatively strong from a mechanical standpoint. When the sleeve 30 is made from a polysulfide, a polysulfide designated as "Ryton R4" by Phillips Petroleum may be used. Such a polysulfide has the advantage of being chemically inert in the patient's body.

A catheter block (or electrical body) 32 made from a suitable material such as stainless steel or titanium or a suitable alloy such as that designated as "Elgiloy" alloy made by Elgin Watch Company or such as that designated as "Haynes 25" by the Haynes Stellite Company is disposed on a mushroomed portion 21a of the bead 21. The body 32 is fused to the mushroomed portion 21a of the bead 21 when the sleeve is heated to a suitable temperature such as approximately 600° F. The electrical body 32 is provided with an aperture 34 so that the terminal pin 18 can extend through the electrical body. The terminal pin 18 is connected electrically to the electrical body as by welding.

The catheter block 32 is provided at one end with a cylindrical bore 36. A terminal lead 38 is disposed in the bore 36 and is clamped against the wall of the electrical body 32 by an adjustable screw 40 which extends through the wall of the electrical body. The terminal lead 38 receives from the terminal pin 18 the signals which are introduced to the heart of the patient to maintain the heart beat at a particular frequency.

When the bead 21 is made from alumina, the terminal pin 18 is bonded initially as by welding to the electrical body 32. The electrical insulation 20 can then be bonded to the inner surface of the ferrule 14 and the other parts including the filter can be assembled. The sleeve 30 is then bonded to the ferrule 14 and the catheter block 32 by heat.

When the sleeve is made from a suitable material such as polysulfide, all of the parts may be initially assembled. For example, the insulation material may be sealed to the terminal pin 18 and the ferrule 14, and the sleeve 30 may be fused to the catheter block 32 and the ferrule 14. Prongs 44 are then pinched against the terminal pin 18 and the terminal pin 18 is then welded or suitably bonded to the catheter block 32.

The invention described above has certain important advantages. It provides a hermetic seal between the terminal pin 18 and the ferrule 14 and between the terminal pin 18 and the lid 10. It also provides a high electrical impedance between the terminal pin 18 and the lid 10 and maintains this impedance because of the hermetic seal produced between the terminal pin 18 and the lid 10 by the bonding of the insulation 20 to these members. It provides within the ferrule a filter which regulates the frequency of the signals introduced from the heart pacemaker to the electrical terminal pin 18 and then into the body of the patient through the lead 38.

The invention described above also has other important advantages. For example, the electrical body 32 can be attached to the terminal pin 18 without bending or breaking the terminal pin or without stressing the hermetic seal provided between the terminal pin and the ferrule 14 by the fusing of the insulation 20 to these members. This hermetic seal is maintained even when the terminal pin 18 is subjected to considerable bending and twisting forces. By providing the arrangement described above and shown in the drawings, mechanical forces imposed upon the catheter block 32 are transferred from the catheter block to the bead 21 and then by the bead to other members including the ferrule 14.

In this way, the lid assembly constituting this invention is capable of withstanding any bending forces and shields the terminal pin 18 from any such bending forces. This causes the hermetic seal in the terminal to be maintained and the high electrical insulation between the terminal pin 18 and the ferrule 14 and between the terminal pin 18 and the lid 10 to be preserved.

The embodiment shown in FIG. 4 is similar to the embodiment shown in FIGS. 1, 2 and 3 and accordingly includes numerical designations similar to those for the previous embodiment. The embodiment shown in FIG. 4 also includes a seal 100 made from a suitable compressible material having insulating properties. Silicone rubber has been found to be entirely adequate for the seal 100. The seal 100 may be disposed above the filter 22 and may be compressed when the spacer 24 is disposed in position against the flange on the ferrule. By compressing the seal 100, the seal presses against the terminal pin 18 and the ferrule 14 and facilitates the production of hermatic seals with these members.

An inductance 102 may be disposed within the seal 100. The inductance may be made from a suitable material such as a ferrite having a high mu or a powdered nickel and may be in the shape of a disc or a doughnut. The inductance 102 cooperates with the capacitive filter 22 to prevent the introduction of extraneous signals to the heart pacemaker. For example, the inductance 102 may be in series with the terminal pin 18 and the capacitance 22 may be disposed electrically between the terminal and ground.

Instead of providing the seal 100 and the inductance 102 as separate elements, particles of material with magnetic properties may be dispersed throughout the compressible material defining the seal. This tends to simplify the manufacture of the seal 100 and the inductance 102.

A suitable hermetic seal 104 may be provided directly above the filter 22. The hermetic seal 104 may be made from a suitable glass or from a material disclosed and claimed in copending application Ser. No. 836,659, filed on Sept. 26, 1977 by me and assigned of record to the assignee of record in this application. The inclusion of the seal 104 facilitates the retention of a high insulating relationship between the terminal pin 18 and the ferrule 14 and the electrical isolation of the filter 22 from the terminal and the ferrule. It also prevents chemicals from the patient's body from affecting the operating characteristics of the terminal.

As will be seen from one embodiment shown in FIG. 4, substantially all of the elements within the lid assembly are disposed below the lid 10. This is advantageous because the elements below the lid 10 are effectively sealed and accordingly are not affected by such atmospheric elements as moisture.

Figure 5:
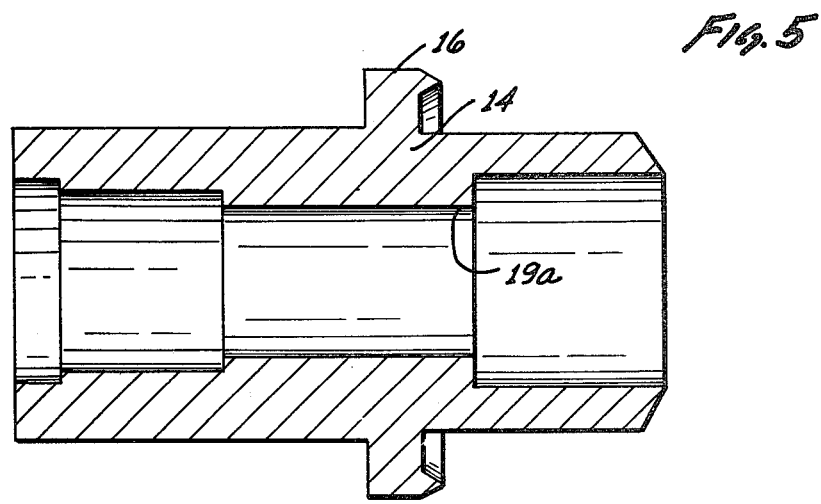
FIG. 5 is a sectional view in a modified form of one of the members shown in FIGS. 2 and 4.

In the embodiment shown in FIG. 5, the internal flange 19 is lengthened axially to define an internal flange 19a. This is desirable because it isolates the filter 22 from the inductance 102 and the other electrical elements in the lid assembly. The seal 100 may be disposed along the axial length of the internal flange 19a to seal the terminal pin 18 and the ferrule 14 hermetically and isolate the other elements in the lid assembly.

Figure 6:
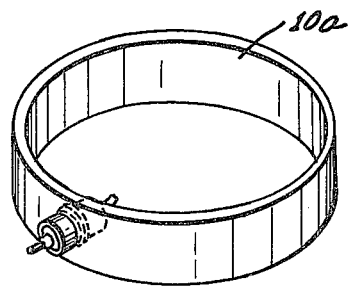
FIG. 6 is a perspective view of another embodiment of a terminal and a lid in assembled relationship.

FIG. 6 illustrates a lid 10a which may be annular in configuration. A terminal pin 18a extends laterally from the side wall of the lid 10a in substantially parallel relationship to the flat surface of the lid.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for providing for the introduction of a terminal lead from a heart pacemaker into the body of a patient, a lid for the heart pacemaker,
an electrical terminal pin,
means supporting the terminal pin in electrically insulated relationship to the lid including
first support means enveloping the electrical terminal pin and disposed in spaced relationship to the terninal pin and engaging the lid,
first insulating means disposed between the terminal pin and the first support means for maintaining the terminal pin in fixed and spaced relationship to the first support means and for providing a long path for the leakage of electrical current between the terminal pin and the lid to maintain the terminal pin in electrically insulated relationship to the lid, and
second insulating means disposed on the first support means and extending from the first support means, and
second support means disposed in electrically communicating relationship with the terminal pin and in insulated relationship with the first support means and supporting the terminal lead for introduction of the electrical signals on the terminal pin to the terminal lead,
the first insulating means providing a hermetic seal between the first support means and the terminal pin and between the lid and the terminal pin.

2. The combination set forth in claim 1 wherein
the electrical terminal pin extends through the second support means is disposed on the first insulating means and wherein the second support means is electrically conductive and includes means engaging the terminal lead and maintaining the terminal lead in fixed relationship to such second support means.

3. The combination set forth in claim 1 wherein the second insulating means provides a support for the second support means.

4. In combination for providing for introduction of a terminal lead from a heart pacemaker into the body of a patient, a lid for the heart pacemaker,
an electrical terminal pin,
a ferrule made from an electrically conductive material and having a hollow configuration and disposed in spaced and concentric relationship to the terminal pin and supported by the lid,
an electrical filter disposed in concentric relationship to the terminal pin and within the ferrule and having properties of passing signals only within a particular range of frequencies,
first means disposed within the ferrule for maintaining the electrical filter in fixed and concentric relationship to the terminal pin and the ferrule,
second means having insulating properties and maintaining the terminal pin and the ferrule in fixed and insulating relationship with a long leakage path between the terminal pin and the ferrule for the flow of electrical current, and third means disposed on the second means and supporting the terminal lead and introducing the electrical signals on the terminal pin to the terminal lead.

5. The combination set forth in claim 4 wherein the second means includes means fused to the ferrule and the terminal pin and the third means and having a thermal coefficient of expansion relative to those of the terminal pin and the ferrule for maintaining this fused relationship with changes in temperature.

6. The combination set forth in claim 5 wherein the fused means are disposed in spaced relationship to the filter and the first means are disposed in the space between the fused means and the filter to maintain the filter in fixed relationship to the terminal, the ferrule and the fixed means.

7. The combination set forth in claim 6 wherein the filter is positioned for disposition at least partially within the heart pacemaker and the ferrule is provided with a flange and the lid is disposed against the flange on the ferrule and is attached to the flange and the ferrule is provided with an internal shoulder and a ring is seated on the shoulder and the fused means is sealed to the ring.

8. The combination set forth in claim 4 wherein a compressible seal is disposed within the ferrule and the seal is compressed by the first means to facilitate the production of a hermetic seal between the terminal pin and the ferrule and the disposition of the filter in the ferrule in a hermetically sealed relationship.

9. The combination set forth in claim 8 wherein an inductance is disposed in the compressible seal and the filter is capacitive and the inductance is connected to the filter to facilitate the passage of signals only within the particular range of frequencies.

10. The combination set forth in claim 4 wherein the filter is positioned for disposition at least partially within the heart pacemaker and the second means includes a bead made from insulating material and the ferrule is provided with a flange and the lid is disposed against the flange on the ferrule and is attached to the flange.

11. In combination for providing for introduction of a terminal lead from a heart pacemaker into the body of a patient,
a lid for the heart pacemaker,
an electrical terminal pin,
a ferrule made from an electrically conductive material and having a hollow configuration and disposed in spaced and concentric relationship to the terminal pin and supported by the lid,
a filter disposed on the terminal pin and within the ferrule in concentric relationship with the ferrule,
means maintaining the electrical terminal pin, the filter and the ferrule in spaced and hermetically sealed and electrically insulating relationship and providing a long path for the flow of leakage current between the terminal pin and the ferrule, and
an electrically conductive catheter block disposed in electrically communicating relationship with the terminal pin and supported by the insulating means and engaging the terminal lead in a fixed relationship to provide for the introduction of electrical signals from the terminal pin to the terminal lead.

12. The combination set forth in claim 11 wherein the electrically conductive catheter block is disposed on the insulating means at a position above the lid and wherein means are provided in the catheter block for maintaining the terminal lead in fixed relationship to the block and in electrically communicating relationship with the block.

13. The combination set forth in claim 12 wherein a compressible seal is disposed within the ferrule between the filter and the insulating means and means are attached to the ferrule to compress the seal for the production of a hermetic seal between the terminal pin and the ferrule.

14. The combination set forth in claim 11 wherein the means maintaining the electrical terminal pin, the filter and the ferrule in spaced relationship includes means fused to the ferrule and the terminal pin and having a thermal coefficient of expansion relative to those of the terminal pin and the ferrule for maintaining this fused relationship with changes in temperature.

15. The combination set forth in claim 14 wherein the fused means is disposed in spaced relationship to the filter and means are disposed in the space between the fused means and the filter to maintain the filter in fixed relationship to the terminal pin, the ferrule and the fused means.

16. The combination set forth in claim 15 wherein the ferrule is provided with an internal shoulder and a ring is disposed on the internal shoulder and the fused means is fused to the ring.

17. The combination set forth in claim 11 wherein an inductance is disposed within the ferrale and is connected electrically to the filter and the filter is provided with capacitive properties.

18. The combination set forth in claim 11 wherein the filter is positioned for disposition at least partially within the heart pacemaker and the ferrule is provided with a flange and the lid is disposed against the flange and is attached to the flange.

19. In combination for use in a heart pacemaker constructed to be disposed in the body of a patient,
a ferrule having electrically conductive properties and having an external flange,
a terminal pin disposed within the ferrule,
means having insulating properties and fused to the terminal pin and the ferrule for maintaining the terminal pin in fixed relationship to the ferrule and for providing a long path for any leakage of electrical current between the terminal pin and the ferrule,
a filter disposed on the terminal pin and within the ferrule in fixed relationship with the ferrule and having properties of passing signals only within a particular frequency range,
means for maintaining the filter on the terminal pin and within the ferrule in fixed relationship with the ferrule, and
a lid disposed on the ferrule against the flange.

20. The combination set forth in claim 19 wherein the ferrule is provided with an internal flange at a position displaced from the lid and the insulating means is disposed against the internal flange.

21. The combination set forth in claim 19 wherein the ferrule is provided with an internal shoulder and a bead is disposed within the ferrule and is seated on the shoulder and is made from a material to facilitate the fusing of the fused means to the bead to maintain the fused relationship between the terminal pin, the ferrule and the bead.

22. The combination set forth in claim 19 wherein a terminal lead is provided for introduction into the body of the patient and support means are disposed on the insulating means for providing an electrical connection from the terminal pin to the terminal lead and for maintaining the terminal lead in supported relationship.

23. The combination set forth in claim 22 wherein the support means includes:
a bead, and
a catheter block made from electrically conductive material and extending through and engaging the terminal pin and disposed on the bead and engaging the terminal lead to provide electrical conductivity from the terminal pin to the terminal lead.

24. In combination for providing for the introduction of a terminal lead from a heart pacemaker into the body of a patient,
a lid for the heart pacemaker,
an electrical terminal pin,
means for supporting the terminal pin in electrically insulated relationship to the lid including
first support means enveloping the electrical terminal pin and disposed in spaced relationship to the terminal pin and engaging the lid,
first insulating means disposed between the terminal pin and the first support means for maintaining the terminal pin in fixed and spaced relationship to the first support means and for providing a long path for the leakage of electrical current between the terminal pin and the lid to maintain the terminal pin in electrically insulated relationship to the lid, and
second insulating means supported by the first support means and extending from the first support means, and
second support means disposed in electrically communicating relationship with the terminal pin and supporting the terminal lead for introduction of the electrical signals on the terminal pin to the terminal lead, and
an electrical filter disposed within the first support means in fixed relationship to the first support means and provided with characteristics to pass to the patient from the heart pacemaker electrical signals having only particular frequencies.

25. The combination set forth in claim 24 wherein the first support means is provided with a flange and the lid is disposed against the flange and is attached to the flange and wherein the electrical filter is positioned for disposition at least partially within the heart pacemaker.

26. The combination set forth in claim 24 wherein the first support means is provided with an internal shoulder and the first insulating means is seated on the shoulder and the first insulating means also includes means fused to the terminal pin and the first support means and having a coefficient of thermal expansion relative to those of the first support means and the terminal path to maintain the first support means and the terminal pin in fused relationship with changes in temperature.

27. The combination set forth in claim 24 wherein the electrical filter is capacitive and an inductance is disposed within the first support means and is connected electrically to the electrical filter to facilitate the passage to the patient from the heart pacemaker only of electrical signals having the particular frequencies.

28. The combination set forth in claim 24 wherein the inductance is disposed in a compressible seal and the seal is compressed when the first support means is disposed in electrically insulated relationship to the lid.

29. In combination for providing for the introduction of signals to a terminal lead in a heart pacemaker,
a lid for the heart pacemaker,
a terminal pin,
a conductive ferrule enveloping the terminal pin in spaced relationship to the terminal pin, the ferrule engaging the lid to position the lid,
a catheter block engaging the terminal pin and supporting the terminal lead to provide for the introduction of signals from the terminal pin to the terminal lead,
first insulating means disposed between the terminal pin and the ferrule and hermetically sealing the terminal pin and the ferrule and hermetically sealing the terminal pin and the lid, and
second insulating means disposed on the terminal pin between the first insulating means and the ferrule and supporting the catheter block in spaced relationship to the ferrule.

30. The combination set forth in claim 29 wherein the ferrule is provided with an internal flange and the first insulating means is disposed on the internal flange.

31. The combination set forth in claim 30 wherein the ferrule and the first insulating means are provided with shoulders and the second insulating means is disposed on the shoulders on the ferrule and the first insulating means.

32. The combination set forth in claim 30 wherein the ferrule is provided with an external flange and the lid is disposed on the external flange.

33. The combination set forth in claim 32 wherein a filter is disposed on the terminal pin and within the ferrule and wherein means are disposed on the terminal pin to maintain the filter in fixed relationship to the terminal pin and the ferrule.

34. The combination set forth in claim 33 wherein the filter is capacitive and an inductance is disposed on the terminal pin and within the ferrule and is connected to the filter to provide a tuned circuit.

35. The combination set forth in claim 34 wherein the filter positioned for disposition within the heart pacemaker and means are included for sealing the filter within the heart pacemaker and wherein the inductance is included within such sealing means.

36. In combination for providing for the introduction of signals to a terminal lead in a heart pacemaker,
a lid for the heart pacemaker,
a terminal pin,
a conductive ferrule enveloping the terminal pin in spaced relationship to the terminal pin, the ferrule abutting the lid and being attached to the lid,
a catheter block disposed on the terminal pin in spaced relationship to the ferrule and the lid and attached to the terminal pin, and
insulating means disposed between the terminal pin and the ferrule and between the ferrule and the catheter block and hermetically sealing the terminal pin relative to the ferrule and the lid and insulating the terminal pin relative to the ferrule and the lid.

37. The combination set forth in claim 36, including, a filter disposed within the ferrule, a spacer disposed within the ferrule between the filter and the ferrule and positioned against the ferrule to provide a particular positioning of the filter relative to the ferrule, and means for rotating the filter in the particular relationship with respect to the ferrule.

38. The combination set forth in claim 36 wherein the filter is disposed below the lid and is capacitive and an inductance is disposed within the ferrule and is electrically connected to the filter to provide a tuned circuit.

39. The combination set forth in claim 36 wherein the insulating means includes a material hermetically sealed to the terminal pin and the ferrule and further includes an insulating bead fused to the insulating material and supporting the catheter block.

40. The combination set forth in claim 39 wherein an insulating sleeve is disposed on the ferrule and the insulating bead extends to a position beyond the ferrule and the insulating sleeve and the insulating bead supports the catheter block at a position beyond the ferrule and the insulating sleeve.

41. The combination set forth in claim 36, including, an insulating sleeve disposed on the ferrule, a filter disposed within the ferrule, and means disposed within the ferrule for maintaining the filter in a particular fixed relationship within the ferrule.

* * * * *